United States Patent
Pettit et al.

(10) Patent No.: US 7,541,346 B2
(45) Date of Patent: *Jun. 2, 2009

(54) PANCRATISTATIN CYCLIC PHOSPHATE PRODRUGS AND PHENPANSTATIN CYCLIC PHOSPHATE PRODRUGS

(75) Inventors: George R. Pettit, Paradise Valley, AZ (US); Noeleen Melody, Mesa, AZ (US)

(73) Assignee: Arizona Board of Regents, a body corporate of the State of Arizona, Acting for and on Behalf of the Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/025,525

(22) Filed: Feb. 4, 2008

(65) Prior Publication Data

US 2008/0139509 A1 Jun. 12, 2008

Related U.S. Application Data (63) Continuation of application No. 10/561,338, filed as application No. PCT/US2004/019725 on Jun. 18, 2004, now Pat. No. 7,351,830.

(60) Provisional application No. 60/480,291, filed on Jun. 20, 2003.

(51) Int. Cl.
*A61K 31/675* (2006.01)
*A61K 31/4741* (2006.01)

(52) U.S. Cl. .......................... 514/89; 514/280; 514/287
(58) Field of Classification Search .................. 514/89, 514/280, 287
See application file for complete search history.

(56) References Cited

U.S. PATENT DOCUMENTS 7,351,830 B2 * 4/2008 Pettit et al. .................... 546/23

FOREIGN PATENT DOCUMENTS

WO      WO 02/50023      6/2002

OTHER PUBLICATIONS

Pettit, G.R. et al.: Antineoplastic agents 500. Narcistatin. J. Nat. Prod., vol. 66, pp. 92-96, 2003.*
International Search Report for PCT/US04/19725 dated Jan. 11, 2005.
Written Opinion of the International Search Authority for PCT/US04/19725 dated Jan. 11, 2005.
Pettit et al., "Antineoplastic Agents. 511. Direct Phosphorylation of Phenpanstatin and Pancratistatin", *J. Nat. Prod.*, 67:322-327, (2004).
Mamber et al., "Tubulin Polymerization by Paclitaxel (Taxol) Phosphate Prodrugs After Metabolic Activation with Alkaline Phosphatase", *The Journal of Pharmacology and Experimental Therapeutics*, 274(2):877-883 (1995).
Shnyder et al., "Sodium Pancratistatin 3,4-O-Cyclic Phosphate, a Water-Soluble Synthetic Derivative of Pancratistatin, is Highly Effective in a Human Colon Tumor Model", *J. Nat. Prod.*, 71:321-324 (2008).

* cited by examiner

*Primary Examiner*—Charanjit S Aulakh
(74) *Attorney, Agent, or Firm*—McAndrews Held & Malloy Ltd.

(57) ABSTRACT

Selective phosphorylation of phenpanstatin (3a) with tetrabutylammonium dihydrogen phosphate and dicyclohexylcarbodiimide in pyridine followed by cation exchange chromatographic procedures was found to provide an efficient route to a new series (3b-3d) of promising 3,4-O-cyclic phosphate prodrugs designated phenpanstatin phosphates. Application of analogous reaction conditions to pancratistatin (1a) led to a mixture of monophosphate derivatives where sodium pancratistatin 4-O-phosphate (4a) was isolated and the structure confirmed by x-ray crystallography. Modification of the reaction conditions allowed direct phosphorylation of pancratistatin followed by cation exchange chromatography to afford sodium pancratistatin 3,4-O-cyclic phosphate (5b) which was selected for preclinical development.

4 Claims, 2 Drawing Sheets

Figure 1. An X-ray thermal ellipsoid plot (50 % probability) of sodium pancratistatin 4-O-phosphate (4a) as the dihydrate.

Figure 2

PANCRATISTATIN CYCLIC PHOSPHATE PRODRUGS AND PHENPANSTATIN CYCLIC PHOSPHATE PRODRUGS

RELATED APPLICATION DATA

This application is a continuation of U.S. Nonprovisional application Ser. No. 10/561,338, filed on Dec. 15, 2005, now U.S. Pat. No. 7,351,830, which is the U.S. national stage of PCT/US2004/019725 filed on Jun. 18, 2004, which is based on and claims the benefit of U.S. Provisional Patent Application No. 60/480,291 filed on Jun. 20, 2003, all of the foregoing which are incorporated herein in their entireties by this reference.

INTRODUCTION

Financial assistance for this invention was provided by the United States Government, Division of Cancer Treatment and Diagnosis, National Cancer Institute, Department of Health and Human Services Outstanding Investigator Grant Numbers CA44344-05-1-12 and R01-CA9044-01; the Arizona Disease Control Research Commission; and private contributions. Thus, the United States Government has certain rights in this invention.

FIELD OF THE INVENTION

This invention relates to novel pancratistatin cyclic phosphate and phenpanstatin cyclic prodrugs, and methods for producing same. The prodrugs exhibit cancer cell inhibitory activity.

BACKGROUND OF THE INVENTION

In 1984, the structure of (+)-pancratistatin (1a), the principal anticancer constituent of the Amaryllidaceae tropical spider lily *Pancratium littorale,* which was later reidentified as *Hymenocallis littoralis,* first isolated and elucidated (by x-ray employing the 7-methoxy derivative) (Pettit, G. R., et al., G. M. Antineoplastic Agents 105, *Zephyranthes grandiflora, J. Nat. Prod.* 1984, 47, 1018-1020; Pettit, G. R., et al., Isolation and Structure of Pancratistatin, *J. Chem. Soc.,* Chem. Commun. 1984, 1693-1694; Pettit, G. R., et al., Antineoplastic Agents, 120. *Pancratium Littorale, J. Nat. Prod.* 1986, 49, 995-1002; Pettit, G. R., et al., Antineoplastic Agents, 301. An Investigation of the *Amaryllidaceae* Genus *Hymenocallis, J. Nat. Prod.* 1995, 58, 756-759.) Because of the early promise of pancratistatin (1a) as a new type of anticancer and antiviral (RNA viruses) drug, various phases of preclinical development have been underway for over seventeen years. (Pettit, G. R., et al., Isolation and Structure of Pancratistatin, *J. Chem. Soc., Chem. Commun.* 1984, 1693-1694; Gabrielsen, B., et al., Antiviral (RNA) Activity of Selected *Amaryllidaceae* Isoquinoline Constituents and Synthesis of Related Substances, *J. Nat. Prod.* 1992, 55, 1569-1581; Pettit, G. R., et al., Antineoplastic Agents 320: Synthesis of a Practical Pancratistatin Prodrug, Anti-Cancer Drug Design 1995, 10, 243-250; Pettit, G. R., et al., Antineoplastic Agents 453. Synthesis of Pancratistatin Prodrugs, *Anti-Cancer Drug Design* 2000, 15, 389-395; Toki, B., et al., Protease-Mediated Fragmentation of p-Amidobenzyl Ethers: A New Strategy for the Activation of Anticancer Prodrugs. *J. Org. Chem.* 2002, 67, 1866-1872.)

Meanwhile, there has been increasing success in developing the availability of pancratistatin (1a) by horticultural and synthetic approaches as well as further defining SAR requirements. (Pettit, G. R., et al., Antineoplastic Agents, 301, An Investigation of the *Amaryllidaceae* Genus *Hymenocallis, J. Nat. Prod.* 1995, 58, 756-759; Pettit, G. R., et al., Antineoplastic Agents 450. Synthesis of (+)-Pancratistatin from (+)-Narciclasine as Relay, *J. Org. Chem.* 2001, 66, 2583-2587; Hudlicky, T., et al., Total Synthesis and Biological Evaluation of *Amaryllidaceae* Alkaloids: Narciclasine, ent-7-deoxypancratistatin, 7-deoxypancratistatin, its 10b-Epimer, and Truncated Derivatives, *J. Org. Chem.,* 2002, 67, 8726-8743; McNulty, J., et al., Studies Directed Towards the Refinement of the Pancratistatin Cytotoxic Pharmacophore. *Bioorg. Med. Chem. Lett.* 2001, 11, 169-172; Pettit, G. R., et al., Synthesis of 10b-R-Hydroxy-Pancratistatin via Narciclasine, *J. Chem. Soc., Chem. Commun.* 1994, 2725-2726.) When the preclinical drug formulation of pancratistatin (1a) began to present another challenge owing to the sparing (53 µg/ml in water) solubility behavior of this isocarbostyril (1a) investigation began into structural modifications that were expected to greatly increase aqueous solubility while serving as a successful delivery-type prodrug. (Pettit, G. R., et al., Antineoplastic Agents 320: Synthesis of a Practical Pancratistatin Prodrug, *Anti-Cancer Drug Design* 1995, 10, 243-250; Toki, B., et al., Protease-Mediated Fragmentation of p-Amidobenzyl Ethers: A New Strategy for the Activation of Anticancer Prodrugs, *J. Org. Chem.* 2002, 67, 1866-1872.) Those studies led to useful syntheses (4 steps) of sodium pancratistatin 7-O-phosphate (1b) with considerably improved aqueous solubility (20 mg/ml). (Pettit, G. R., et al., Antineoplastic Agents 320: Synthesis of a Practical Pancratistatin Prodrug, *Anti-Cancer Drug Design* 1995, 10, 243-250; Pettit, G. R., et al., Antineoplastic Agents 453. Synthesis of Pancratistatin Prodrugs, *Anti-Cancer Drug Design* 2000, 15, 389-395.)

While the 7-O-phosphate (1b) proved to have attractive aqueous solubility properties, the yield penalizing synthetic steps from pancratistatin (1a) required continuation of parallel efforts to directly, but selectively, phosphorylate pancratistatin (1a). The necessity of discovering more efficient techniques for converting pancratistatin (1a) to very effective phosphate prodrugs has been accelerating with the recent realization that the long elusive key mechanism of action by isocarbostyril 1a against in vivo neoplastic disease is cancer antiangiogenesis/vascular targeting. (Bibby, M. C., et al., Anti-Vascular and Anti-Tumour Effects of the Novel Agent Pancratistatin Phosphate. Biological Basis for Antiangiogenic Therapy Conference, Milan, Italy, Nov. 8-10, 1999.) Furthermore, pancratistatin (1a) has also recently been found to display remarkable activity against microspirochesis, another potentially lethal challenge for some cancer patients. (Ouarzane-Amara, M., et al., In Vitro Activities of Two Antimitotic Compounds, Pancratistatin and 7-Deoxynarciclasine, against *Encephalitozoon intestinalis,* a Microsporidium Causing Infections in Humans, *Antimicrob. Agents Chemother.* 2002, 45, 3409-3415.)

SUMMARY OF THE INVENTION

Disclosed herein are several new series of compounds, and methods for producing same. Described herein is a new series of promising 3,4-O-cyclic phenpanstatin phosphate prodrugs, a new series of promising 3,4-O-cyclic pancratistatin phosphate prodrugs, and a new series of promising 4-O-sodium pancratistatin phosphate prodrugs. Also disclosed herein are methods for synthesizing these new compounds.

The method for synthesizing compounds 3b, 3c and 3d involves selective phosphorylation of phenpanstatin (3a) with tetrabutylammonium dihydrogen phosphate and dicyclohexylcarbodiimide in pyridine followed by cation exchange chromatographic procedures was used. The method for synthesizing compounds 5a, 5b and 5c involves the application of analogous reaction conditions to pancratistatin (1a) led to a mixture of monophosphate derivatives where sodium pancratistatin 4-O-phosphate (4a) was isolated and the structure confirmed by x-ray crystallography. Modification of the reaction conditions allowed direct phosphorylation of pancratistatin followed by cation exchange chromatography to afford sodium pancratistatin 3,4-O-cyclic phosphate (5a).

DETAILED DESCRIPTION OF THE INVENTION

Materials and Methods

Toward the objective of efficiently phosphorylating pancratistatin (1a), the more abundant but closely related *Amaryllidaceae* biosynthetic product narciclasine (2a), which also required conversion to a phosphate prodrug for anticancer preclinical development, served as a model for most of the exploratory phosphorylation experiments. (Khorana, H. G., et al., The Reaction Between Carbodiimides and Acid Esters of Phosphoric Acid. A New Method for the Preparation of Pyrophosphates, *J. Chem. Soc.* 1953, 2257-2260; Khorana, H. G. Carbodiimides. V. A Novel Synthesis of Adenosine Di-and Triphosphate and P1, *J. Amer. Chem. Soc.* 1954, 76, 3517-3522; Dekker, C., et al., Carbodiimides. VI. The Reaction of Dicyclohexylcarbodiimide with Yeast Adenylic Acid. A New Method for the Preparation of Monoesters of Ribonucleoside 2'- and 3'-Phosphates, *J. Amer. Chem. Soc.* 1954, 76, 3522-3527; Tener, G. M. 2-cyanoethyl Phosphate and its Use in the Synthesis of Phosphate Esters, *J. Amer. Chem. Soc.* 1961, 83, 159-168.)

Eventually reaction conditions were found for efficient phosphorylation of narciclasine (2a) with tetrabutylammonium dihydrogen phosphate using dicyclohexylcarbodiimide (DCCI) in pyridine containing p-toluenesulfonic acid to yield the very useful 3,4-O-cyclic phosphate 2b as a pyridinium salt that separated from the reaction mixture. (Pettit, G. R., et al., Antineoplastic Agents 500. Narcistatin. *J. Nat. Prod.*, 2003, 66, 92-96.) By application of ion-exchange methods, the pyridinium salt was easily converted to a series of metal and ammonium cation derivatives. (Pettit, G. R., et al., Antineoplastic Agents 500. Narcistatin, *J. Nat. Prod.*, 2003, 66, 92-96.)

When the preceding direct phosphorylation reaction was applied to phenpanstatin (3a), another of the pancratistatin series we have in preclinical development that required a suitable phosphate derivative, the main product was again the 3,4-O-cyclic phosphate (3b). (Pettit, G. R., et al., Antineoplastic Agents 450. Synthesis of (+)-Pancratistatin from (+)-Narciclasine as Relay, *J. Org. Chem.* 2001, 66, 2583-2587.) The crude tetrabutylammonium salt was converted by ion exchange→LH-20 Sephadex chromatographic separation series to the corresponding sodium salt designated sodium phenpanstatin (3b) and subsequently to the Li$^+$ and K$^+$ cation derivatives 3c and 3d. The 3,4-O-cyclic phosphate structure (3b) was well supported by the NMR spectra with the $^{31}$P-NMR shift well downfield at 13.0 ppm close (δ 20.3) to that of 3,4-O-cyclic phosphate 2b where the structure was confirmed by x-ray crystal structure determination as well as by other evidence that now follows.

Detailed analysis of the $^1$H, $^{13}$C, COSY, HMQC, and D$_2$O exchange experiments was carried out in an effort to assign the carbon and proton spectrum. A downfield shift of the ring protons H-3 and H-4 was observed when compared with the $^1$H spectrum of the starting material phenpanstatin (3a). There were no OH-3 and OH-4 signals observed in the spectrum. The signal for the OH-2 proton was observed downfield at 6.13 ppm as a broad singlet which disappears when a D$_2$O exchange experiment was performed.

Analysis of the COSY spectrum indicated the H-1 signal was downfield at 5.73 ppm as expected, showing strong correlation peaks with the signals at 4.19 and 3.3 ppm for H-2 and H-10b, respectively. The H-2 signal in turn correlated with the signal at 4.32 ppm (H-3). The H-10b signal correlated with the signal at 4.41 ppm (H-4a). The signal at 4.25 ppm was assigned to H-4. The OH-2 signal at 6.13 ppm showed a correlation peak with the signal assigned to H-2 at 4.19 ppm. The D$_2$O exchange experiment resulted in a downfield shift of the water peak which allows one to see the signal for H-10b at 3.27 (D$_2$O/DMSO-d$_6$) as a broad doublet. The $^{13}$C spectrum was examined using HMQC. There was a noticeable downfield shift of the C-3 and C-4 signals from 68.8 in the $^{13}$C spectrum of phenpanstatin to 74.8 (C-3) and 74.9 (C-4) in the cyclic phosphate (3b), further proof that the cyclic phosphate had been prepared.

The lithium and potassium salts 3b and 3c were prepared by passing the sodium salt through an ion exchange column of the respective cation.

When the tetrabutylammonium dihydrogen phosphate reaction was applied to phosphorylation of pancratistatin (1a) using the procedure that provided 3,4-O-cyclic phosphates 2b and 3b, the result was quite different and presumably owing to the unprotected 1-hydroxy group. The reaction was performed at 80° C. over five days and appeared complete by 300 MHz NMR analysis at that point. The mixture of pancratistatin phosphate salts was converted to the sodium salts for ease of separation using an ion exchange (Dowex 50W X8 200, Na$^+$ form)→Sephadex G-10 sequence. The phosphates were retained in preference to other components on the G-10 Sephadex column and further separation by recrystallization of the phosphate mixture from water-methanol yielded (3.7%) pancratistatin 4-O-phosphate (4a, $^{31}$P-NMR δ 4.73). The second and third crops of crystals and the mother liquor residue were found to be mixtures ($^{31}$P δ 6.81, 6.00, 4.90 and 3.26) of phosphates.

Detailed NMR analysis was carried out in an attempt to establish the position of the phosphate (4a). The ring protons were assigned using a COSY spectrum where H-10b (δ 2.96) showed strong correlation signals with a H-4a (δ 3.74) and H-1 (4.24). In turn, H-4a exhibited strong correlation signals with H-4 (δ 4.29). The H-3 and H-2 resonances were assigned to the narrow multiplet at δ 3.95 integrating for 2 hydrogens. The correlation peaks associated with this multiplet were in accord with those predicted. A D$_2$O exchange NMR experiment led to elimination of the four signals at δ 13.34 (phenolic OH), 10.22 (NH), 4.74-4.72 (OH), and 3.47 (OH). The OH resonance at δ 4.73 gave a strong correlation peak in the COSY spectrum with the resonance assigned to H-1. Therefore, this signal was assigned to OH-1. A $^{31}$P NMR spectrum displayed one signal at δ 4.73, implying one phosphorous atom per molecule. An x-ray crystal structure determination was required to confirm the structure of sodium phosphate 4a. Recrystallization of phosphate 4a from water-methanol provided a crystal suitable by crystallography.

The cyclic phosphate of pancratistatin (5a) was eventually prepared following a series of exploratory experiments by reducing the tetrabutylammonium dihydrogen phosphate from 8 equiv to 1.9 equivalents and maintaining an excess of dicyclohexylcarbodiimide. The paratoluene sulfonic acid was also reduced from 3 to 1.3 equivalents. The reaction goes to completion overnight at 80° C. to yield one product by $^1$H NMR. This method was found to be low yielding as the workup caused decomposition of the cyclic phosphate to a 2:1 ratio of 5a:4a. Recrystallization from methanol:dichloromethane yielded pure cyclic phosphate (28%); however, further purification of the mother liquor containing a mixture of 5a, 4a and sodium tosylate was not achieved. The cyclic phosphate 5a was eventually prepared in high yield (48% following recrystallization from water:methanol:dichoromethane) when the paratoluene sulfonic acid was not added and the reaction was allowed to proceed for 48 hours with additional amounts of dicyclohexylcarbodiimide and tetrabutylammoniumdihydrogen phosphate being added after 24 hours.

Detailed NMR analysis using $^1$H, $^{13}$C, COSY, HMQC and $D_2O$ exchange experiments were carried out to confirm the 3,4 position of the cyclic phosphate. Analysis of the product by $^{31}$P NMR shows a phosphorous peak downfield at 13.22 (DMSO-$d_6$) which indicates the presence of a cyclic phosphate group. A $D_2O$ exchange experiment showed exchangeable peaks to be at 13.25, 8.10, 5.42, and 4.69 ppm, OH-7, N—H, OH-2 and OH-1, respectively. The COSY spectrum revealed strong correlation peaks between the multiplets at 2.85 (H10b), 4.27 (H-1) and 4.09 (H-4a) ppm. The peak at 4.02 ppm was assigned to H-2 due to the correlation peaks observed with H-1 and the OH peak at 5.42 ppm. The multiplet at 4.21 could be assigned to H-3 due to crosspeaks observed with the H-2 peak at 4.02 ppm. The multiplet at 4.08-4.04 contains the H-4 signal.

The $^1$H NMR spectrum of 5a was compared with the $^1$H NMR spectrum of pancratistatin. Downfield shifts of the H-3, H-4 and H-4a signals by 0.38, 0.36 and 0.36 ppm, respectively, were observed. The downfield shifts observed for H-1 and H-2 were relatively minor, 0.01 and 0.08 ppm, respectively. This proves that the cyclic phosphate was in the 3,4 position.

The lithium and potassium salts 5b and 5c were prepared by passage through an ion exchange column containing the respective ion. When the cyclic phosphate 5a was passed through an ion exchange column (H+ form) in an effort to prepare the cyclic phosphoric acid, it decomposed to the 4-O-phosphoric acid (4b). This development led to the preparation of the 4-O-phosphate salts 4c-4l.

The lithium salt (4c) was prepared by passing it through a column containing Dowex 50WX8-200 cation exchange resin containing the respective cation. The potassium salt was then prepared from the lithium salt by dissolving 4c in water and passing it through a column containing Dowex 50WX8-200 cation exchange resin (K+form).

The magnesium (4d), calcium (4e) and zinc (4f) salts were obtained by dissolving the phosphoric acid 4b in methanol and adding one equivalent of the respective metal acetate. The resulting opaque solutions were stirred for several days as the salt precipitated from solution. The mixture was then concentrated and the salts washed with methanol. A selection of ammonium salts were prepared by allowing the phosphoric acid 4b to react with the respective amine at room temperature. The reaction mixture was concentrated and the solid washed with a suitable solvent to give the ammonium salts 4h-4l.

The new pancratistatin and phenpanstatin phosphate prodrug series was evaluated against a minipanel of human cancer cell lines and the murine P388 lymphocytic leukemia cell line. Results of the cancer cell line evaluations compared to the parent pancratistatin (1a) and phenpanstatin (3b) appear in Table 1 and confirm retention of cancer cell line inhibitory activity comparable to the respective anticancer drug.

Experimental Section (+)-Pancratistatin (1a) was isolated from *Hymenocallis littoralis* as previously described. (Pettit, G. R., et al., Antineoplastic Agents, 301, An Investigation of the *Amaryllidaceae* Genus *Hymenocallis*. J. Nat. Prod. 1995, 58, 756-759.) Reagents were purchased from Acros chemical company unless otherwise noted and used as received. Solvents were distilled prior to use and pyridine preceding distillation was dried over potassium hydroxide pellets. The pancratistatin containing derivatives were visible as green-blue fluorescent spots on TLC plates under long wave ultraviolet light. Dowex 50WX8-200 cation exchange resin (H+ form) was washed with methanol, 1N hydrochloric acid and deionized water. The cation forms of the resin were obtained by washing with a 1N solution of the appropriate base followed by deionized water.

Melting points were determined using a Fisher-Johns melting point apparatus and are uncorrected. Thin layer chromatography was performed on Analtech silica gel GHLF plates. High resolution FAB spectra were obtained using a JEOL LCMate magnetic sector instrument in either the FAB mode, with a glycerol matrix, or by APCI with a polyethylene glycol reference or by Washington University Mass Spectrometry Resource. All $^1$H-NMR spectra were initially obtained using a Varian Gemini 300 MHZ instrument unless otherwise noted. The $^{13}$C, $^1$H-$^1$H COSY, $^1$H-13C HMBC, $^1$H-$^{13}$C HMQC, and $^{31}$P NMR experiments were conducted employing a Varian Unity 400 and 500 MHz instrument.

Sodium Phenpanstatin 3,4,O-cyclic Phosphate (3b)

Phenpanstatin (0.20 g, 0.26 mmol) was dissolved in pyridine (10 ml) and the solution heated to 80° C. under argon before adding tetrabutylammonium dihydrogen phosphate (1.25 g, 3.68 mmol, 8 equiv), dicyclohexylcarbodiimide (1.20 g, 5.8 mmol, 12.6 equiv) and paratoluenesulfonic acid (0.26 g, 1.36 mmol, 3 equiv). The reaction was monitored by $^1$H NMR (DMSO-$d_6$) and after 24 hours the NMR spectrum showed a 50:50 mixture of starting material to product. Dicyclohexylcarbodiimide (0.425 g) was added and the reaction continued for a total of 48 hours.

The mixture was cooled, and the dicyclohexylurea (DCU) precipitate was collected and washed with water. Additional water (100 ml) was added to the mother liquor and the DCU again collected. The mother liquor was extracted with butanol (2×40 ml) and the butanol fractions combined and concentrated to a light brown oil. A solution of the oil in water (minimum amount) was purified through a column of Dowex 50WX8-200 ion exchange column (Na+ form) (14 cm×2 cm). The UV active fractions were combined and freeze dried to yield a white solid which was further purified in methanol on a Sephadex LH-20 column (70 cm×2 cm, eluent methanol at 1.8 ml/min). The product was found to be in tubes 23-40 using tlc (BuOH:MeOH:$H_2O$:$NH_4OH$, 4:3:2:1). These fractions were combined and concentrated to a white solid, 0.145 g, 60%, mp=268° C. dec., $[\alpha]_D$=−51.8° C. (c 0.5, $CH_3OH$), $R_f$=0.69 (BuOH:MeOH:$H_2O$:$NH_4OH$, 4:3:2:1). $^1$H NMR (400 MHz, DMSO-$d_6$) δ 13.25 (s, 1H), 8.52 (s, 1H), 8.1 (d, J=7.6 Hz, 1H), 7.59 (t, J=74 Hz, 1H), 7.41 (t, J=7.6 Hz, 2H), 6.30 (s, 1H), 6.13 (bs, 1H), 6.01 (s, 1H), 5.96 (s, 1H), 5.73 (s, 1H), 4.41 (dd, J=13.2 Hz, J+8.4 Hz, 1H), 4.32-4.21 (m, 2H), 4.11 (bs, 1H), 3.33 (m, 1H) ppm. $^{13}$C NMR (400 MHz, DMSO-$d_6$) δ 169.2, 165.4, 152.1, 145.8, 133.4, 133.3, 132.3, 130.2 (2C), 129.2, 128.7, 107.4, 101.9, 95.8, 74.9, 74.8, 69.1, 66.3, 66.1, 51.3, 35.7 ppm; and $^{31}$P NMR (DMSO-d$_6$) 12.99 ppm. HRFAB: M/2 Found 490.0540 (M–Na)$^-$ C$_{21}$H$_{17}$NO$_{11}$P requires 490.05392 (M–Na)$^-$.

General Procedure for Preparation of the Phenpanstatin Phosphate Prodrugs (3c-3d)

Sodium phenpanstatin 3,4-cyclic phosphate (6 mg) was dissolved in water (0.5 ml) and eluted with water through a column (1 cm×5 cm) of Dowex 50WX8-200 ion exchange resin (respective cation). The UV active fractions were combined and freeze dried to give the corresponding phenpanstatin phosphate prodrug.

Lithium Phenpanstatin 3,4-cyclic Phosphate (3c)

Glassy solid, 4 mg, mp=280° C., $^1$H NMR (300 MHz, CD$_3$OD) δ 8.05 (d, J=5.1 Hz, 2H), 7.53 (t, J=7.35 Hz, 1H), 7.42 (t, J=7.35 Hz, 2H), 6.39 (s, 1H), 5.96 (s, 1H), 5.90 (s, 1H), 4.61-4.51 (m, 3H), 4.33 (bs, 1H), 3.44 (m, 1H) ppm.

Potassium Phenpanstatin 3,4-cyclic Phosphate (3d)

White solid, 3.9 mg, mp 245° C., $^1$H NMR (300 MHz, CD$_3$OD) δ 8.05 (d, J=7.2 Hz, 2H), 7.53 (t, J=7.5 Hz, 1H), 7.42 (t, J=7.65 Hz, 2H), 6.39 (s, 1H), 5.96 (s, 1H), 5.90 (s, 2H), 4.62-4.51 (m, 3H), 4.33 (bs, 1H), 3.46-3.41 (m, 1H) ppm.

Sodium Pancratistatin 4-O-phosphate (4a)

Pancratistatin (1a, 0.2 g, 0.615 mmol) was added to pyridine (10 ml) and the solution was heated. Next, tetrabutylammonium dihydrogen phosphate (1.67 g, 4.92 mmol, 8 equiv), dicyclohexylcarbodiimide (1.01 g, 4.92 mmol, 8 equiv) and p-toluenesulfonic acid (0.35 g, 1.84 mmol, 3 equiv) were added. The resulting solution was stirred under argon and monitored by $^1$H-NMR at 80° C. for two days. As starting material was still present in the reaction mixture, additional DCCI (0.5 g) was added. The mixture was stirred and heated (80°) for a total of 5 days. After adding water (100 ml), dicyclohexylurea precipitated. The mixture was stirred for 1 hour, the solution filtered and concentrated to a brown oil. A solution of the oil in the minimum amount of water was passed through an ion exchange column 12 cm×3.5 cm (Dowex 50WX8-200, sodium form) and eluted with water. The u.v. active fractions were combined according to tlc mobility (n-BuOH-CH$_3$OH—H$_2$O—NH$_4$OH, 4:3:2:1) to give a crude white solid with considerable impurities (0.83 g). After further separation in water on a G-10 Sephadex column (60 cm×2 cm) and elution with water, the 254 fractions collected (at 10 ml/8 min) were again combined according to the tlc data (n-BuOH-CH$_3$OH—H$_2$O:NH$_4$OH, 4:3:2:1). Sodium pancratistatin 4-O-phosphate was found in fractions 41-88 and crystallized from a concentrated solution of these fractions in water-methanol to afford 4-O-phosphate 4a as a colorless solid, insoluble in methanol: wt 9.2 mg, (3.7% yield), m.p. 280° C. dec. $^1$H NMR (500 MHZ, DMSO-d$_6$) δ 13.34 (s, 1H, Ph-OH), 10.2 (bs, 1H, NH), 6.45 (s, 1H, Ar—H), 6.03 (S,1H,) 5.99 (S, 1H,) 4.74-4.72 (m, 1H, OH), 4.29-4.24 (m, 2H), 3.95 (narrow m, 2H), 3.74 (dd, J=13.6 Hz, H-4a), 3.47 (bm, 2H, OH), 2.96 (m, 1H. H-106); $^{13}$C (500 MHZ, DMSO-d$_6$) δ 168.6, 151.6, 145.3, 135.6, 131.6, 107.9, 101.5, 97.6, 72.7, 72.1, 69.9, 68.5, 50.2, 39.8 ppm; $^{31}$P (500 MHZ, DMSO-d$_6$), δ 4.73 ppm. A second and third crop (21 mg) was found to be a mixture of several phosphates when analyzed by $^{31}$P NMR, and the mother liquor was found to be a mixture (39 mg) of two for a total of 79.6 mg (32%). The remaining material on the column visible by UV long wave light was eluted using a gradient of methanol-water to methanol and was identified by NMR as a narciprimine derivative (27 mg) pointing to aromatization of the cyclitol ring during this phosphorylation reaction.

X-Ray Crystal Structure Determination. Sodium pancratistatin 4-O-phosphate (4a) hydrate: A long, colorless, rod-shaped crystal (~0.58×0.16×0.13 mm), grown from a methanol-water solution, was mounted on the tip of a glass fiber. Cell parameter measurements and data collection were performed at 123±2° K on a Bruker SMART 6000 diffractometer. Final cell constants were calculated from a set of 8435 reflections from the actual data collection. Frames of data were collected in the θ range of 5.59 to 69.67° (−8≦h≦8, −17≦k≦17, −18≦1≦19) using 0.396° steps in ω such that a comprehensive coverage of the sphere of reflections was performed. After data collection, an empirical absorption correction was applied with the program SADABS. (Blessing, R., Acta Cryst. 1995, A51, 33-8.) Subsequent statistical analysis of the complete reflection set using the XPREP program indicated the space group was P2$_1$2$_1$2$_1$. (Pettit, G. R., et al., G. M. Antineoplastic Agents 105. *Zephyranthes grandiflora, J. Nat. Prod.* 1984, 47, 1018-1020; Pettit, G. R., et al., Isolation and Structure of Pancratistatin, *J. Chem. Soc.,* Chem. Commun. 1984, 1693-1694; Pettit, G. R., et al., Antineoplastic Agents, 120. *Pancratium Littorale, J. Nat. Prod.* 1986, 49, 995-1002.)

Figure 1:
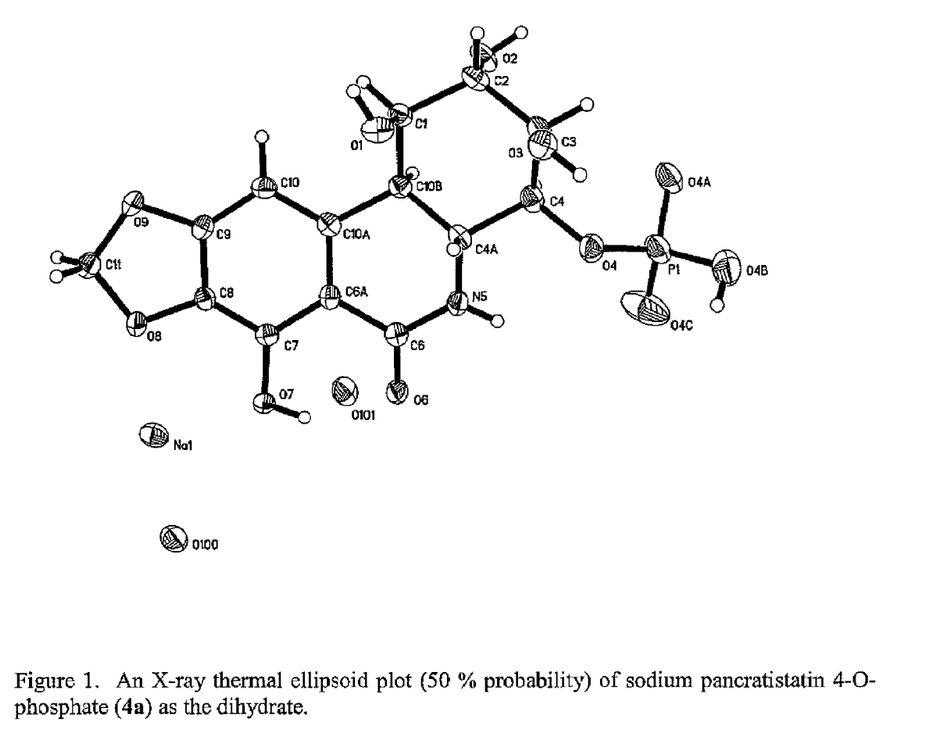
FIG. 1 illustrates an x-ray thermal ellipsoid plot (50% probability) of sodium pancratistatin 4-O-phosphate (4a) as the dihydrate.
Figure 2:
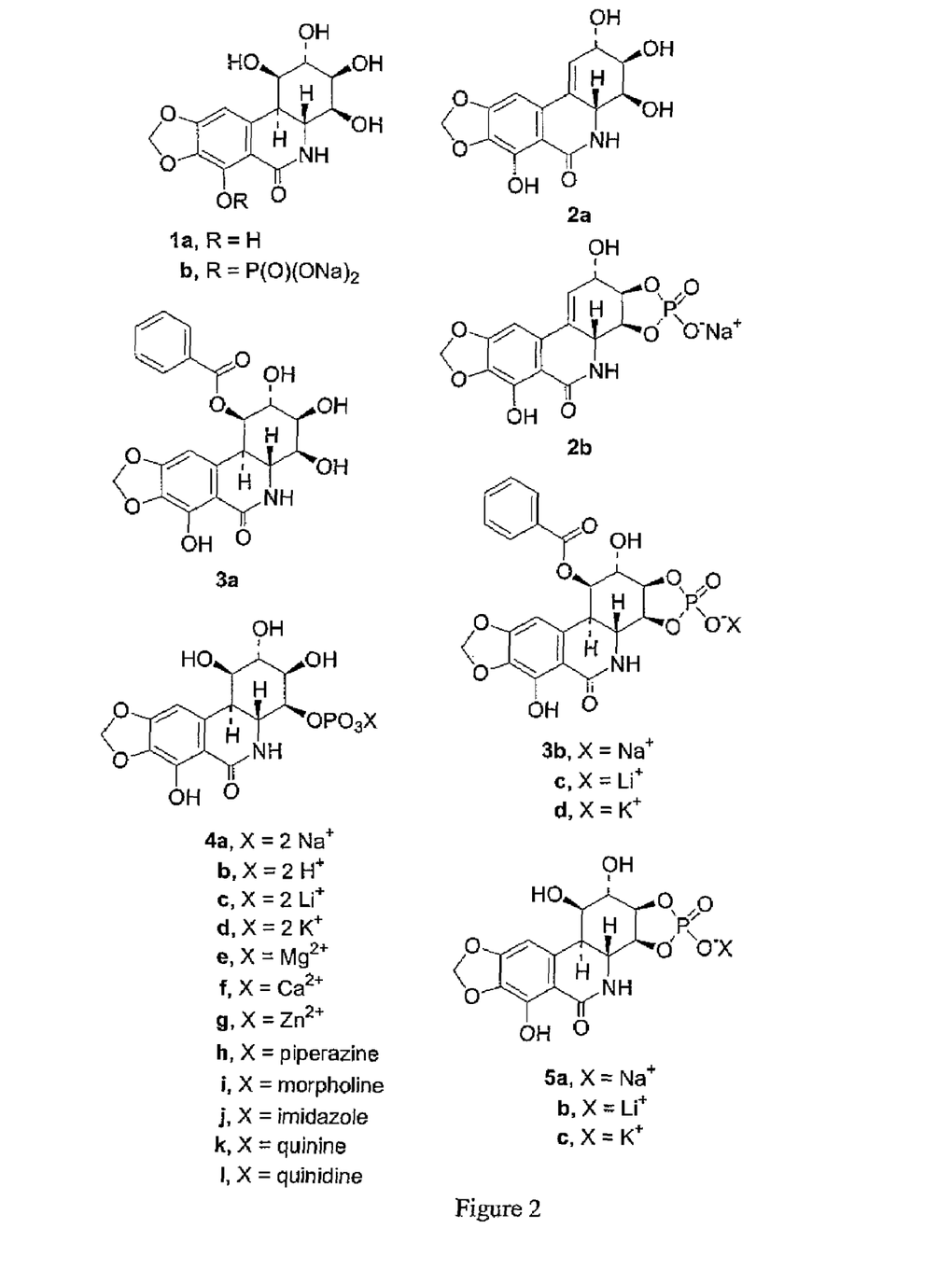
FIG. 2 illustrates various prior art compounds and compounds of the present invention.

Crystal data: C$_{14}$H$_{15}$NNaO$_{11}$P·2 H$_2$O (hydrate), a=7.35630(10), b=14.6555(2), c=15.8310(2) Å, V=1706.74 (4) Å$^3$, λ=(Cu Kα)=1.54178 Å, ρ$_c$=1.803 9 cm$^{-3}$ for Z=4 and F.W.=436.26, F(000)=960. A total of 12108 reflections were collected, of which 3026 were unique (R$_{int}$=0.0366), and 2918 were considered observed (I$_o$>2σ(I$_o$)). These were used in the subsequent structure solution and refinement with SHELXTL-V5.1. ("*SHELXTL-Version* 5.1 (1997)", an integrated suite of programs for the determination of crystal structures from diffraction data, is available from Bruker AXS, Inc., Madison, Wis. 53719, USA. This package includes, among others, XPREP (an automatic space group determination program), SHELXS (a structure solution program via Patterson or direct methods), and SHELXL (structure refinement software).) All non-hydrogen atoms for 4a were located using the default settings of that program. Hydrogen atoms were placed in calculated positions, assigned thermal parameters equal to either 1.2 or 1.5 (depending upon chemical type) of the Uiso value of the atom to which they were attached, then both coordinates and thermal values were forced to ride that atom during final cycles of refinement. All non-hydrogen atoms were refined anisotropically in a fill-matrix least-squares refinement process. In addition to the parent sodium phosphate salt, two additional molecules of water solvent were also present in the asymmetric unit. The final standard residual R$_1$ value for the model shown in FIG. 1 converged to 0.0438 (for observed data) and 0.0453 (for all data). The corresponding Sheldrick R values were wR$_2$ of 0.1205 and 0.1221, respectively and the GOF=1.062 for all data. The difference Fourier map showed residual electron density; the largest difference peak and hole being +0.682 and −0.404 e/Å$^3$, respectively. The Flack absolute structure parameter for the model in FIG. 1 refined to −0.04 (4), indicating that the absolute structure for the enantiomer shown is correct. Final bond distances and angles were all within acceptable limits.

Pancratistatin 4-O-phosphoric Acid (4b)

Sodium pancratistatin 3,4-cyclic phosphate (5a, 0.0165 g, 0.04 mmol) was dissolved in water (1 ml) and eluted through a column containing Amberlite IR 120 (H+) resin. The uv active fractions were combined and freeze dried, 0.011 g, 69%, mp. 150° C. (dec). The material was found to be unstable and decomposed over several days. $^1$H NMR (DMSO-d$_6$, 300 MHz) δ 12.9 (s, 1H), 8.12 (s, 1H), 6.49 (s, 1H), 6.04-6.02 (m, 2H), 4.43 (m, 1H), 4.30 (m, 1H), 3.98-3.87 (m, 3H), 3.07-3.01 (m, 1H).

Lithium Pancratistatin 4-O-phosphate (4c)

Sodium pancratistatin 3,4-cyclic phosphate (5a, 0.144 g, 0.35 mmol) was dissolved in water (1 ml) and eluted on an IR-120 (H+) ion exchange resin to convert to the monophosphoric acid and the uv active fractions were then taken and directly eluted through a Dowex 50WX8-200 ion exchange resin (Li+) form. The UV active fractions were combined and freeze dried to yield a white solid which was taken up in hot methanol and filtered, 0.083 g, etc. 62% yield, Mpt. 265° C., $^1$H NMR (DMSO-d$_6$, 300 MHz) δ 13.3 (s, 1H), 10.3 (s, 1H), 6.44 (s, 1H), 6.02 (s, 1H), 5.98 (s, 1H), 4.76 (m, 1H), 4.26-4.23 (m, 2H), 3.94 (nm, 2H), 3.74 (m, 1H), 2.98-2.93 (m, 1H). $^{13}$C NMR (DMSO-d$_6$, 400 MHz) 168.6, 151.6, 145.3, 135.5, 131.6, 107.9, 101.5, 97.6, 76.7, 72.1, 69.9, 68.5, 50.2, 48.6. $^{31}$P NMR (DMSO-d$_6$, 400 MHz) 2.57 ppm. HRESI m/z found 404.0383 (M−2Li+H)$^-$, $C_{14}H_{15}O_{11}NP^-$ requires 404.0391 (M−2Li+H)$^-$.

Potassium Pancratistatin 4-O-phosphate (4d)

Lithium pancratistatin 4-O-phosphate (0.08 mg) was eluted through an IR-120 (K+) ion exchange resin and the WV active fractions collected and freeze dried, wt. g 0.006, mpt. 230° C. $^1$H NMR (DMSO-d$_6$/D$_2$O) δ 6.42 (s, 1H), 5.99-5.96 (m, 2H), 4.20 (m, 2H), 3.99 (m, 1H), 3.94 (m, 1H), 3.84 (m, 1H), 2.99-2.93 (m, 1H).

General Procedure for the Preparation of the Pancratistatin 4-O-Phosphate Divalent Cation Salts (4e-4g)

The phosphoric acid 4b (0.036 g, 0.086 mmol) was taken up in methanol (3 ml). A 1 ml aliquot of this solution was added to a r.b. flask containing 1 equivalent of the corresponding metal acetate. The opaque solutions were allowed to stir for several days before concentrating to a residue which was washed with methanol, and dried.

Magnesium Pancratistatin 4-O-Phosphate (4e)

Beige solid, 0.010 g, 255 ° C. (dec), insoluble in DMSO-d$_6$, and D$_2$O. HRESI m/z found 404.0368 (M−Mg+H)$^-$, $C_{14}H_{15}O_{11}NP$ requires 404.0392, (M−Mg+H)$^-$.

Calcium Pancratistatin 4-O-Phosphate (4f)

Grey solid, 0.011 g, mpt. 290° C., $^1$H NMR (DMSO-d$_6$, 300 MHz), δ 13.2 (s, 1H), 9.65 (s, 1H), 6.45 (s, 1H), 6.02-5.99 (m, 2H), 4.96 (m, 1H), 4.34-4.26 (m, 2H), 3.96 (m, 2H), 3.85-3.73 (m, 1H), 3.02-2.97 (m, 1H).

Zinc Pancratistatin 4-O-Phosphate (4g)

Crystalline powder, 0.0085 g, mpt. 270° C. (dec), insoluble in DMSO-d$_6$, and D$_2$O. HRESI m/z found 404.0372 (M−Zn+H)$^-$, $C_{14}H_{15}O_{11}NP$ requires 404.0392, (M−Zn+H)$^-$.

General Procedure for the Preparation of the Pancratistatin 4-O-Phosphate Ammonium Salts (4h-4l)

Pancratistatin 4-O-phosphoric acid 4b (0.012 g, 0.03 mmol) was dissolved in methanol (1 ml) and the amine (1.2 equivalent) was added with stirring at room temperature. The reaction was stirred for 4 days before concentrating to a residue which was washed with methanol and the solid filtered and dried.

Piperazinium Pancratistatin 4-O-Phosphate (4h)

Off-white solid, 0.011 g, mpt. 180° C., $^1$H NMR (DMSO-d$_6$, 300 MHz) δ 13.3 (s, 1H), 10.1 (s, 1H), 6.44 (s, 1H), 6.02-5.99 (m, 2H), 4.26-4.24 (m, 2H), 3.94 (m, 2H), 3.73 (m, 1H), 2.98-2.88 (m, 9H). HRESI m/z found 492.1383 (M+H)$^+$, $C_{18}H_{27}O_{11}N_3P$ requires 492.1383 (M+H)$^+$.

Morpholinium Pancratistatin 4-O-Phosphate (4i)

Hydroscopic solid, 0.01 g, mpt. 130° C., $^1$H NMR (DMSO-d$_6$, 300 MHz) δ 13.2 (bs, 1H), 9.93 (s, 1H), 6.45 (s, 1H), 6.03-5.99 (m, 2H), 5.19 (bm, 3H), 4.29-4.24 (m, 2H), 3.95 (nm, 2H), 3.75-3.63 (m, 5H), 2.99-2.86 (m, 5H).

Imidazolium Pancratistatin 4-O-Phosphate (4j)

Crystalline solid, 0.007 g, mpt. 125° C., $^1$H NMR (DMSO-d$_6$, 300 MHz) δ 13.2 (s, 1H), 9.5 (bs, 1H), 7.93 (s, 2H), 7.21 (bs, 4H), 6.45 (s, 1H), 6.03-5.99 (m, 2H), 4.57-4.25 (m, 2H), 3.95 (m, 2H), 3.8 (m, 1H), 3.01-2.97 (m, 1H).

Quinium Pancratistatin 4-O-Phosphate (4k)

Beige solid, 0.015 g, mpt. 173° C., $^1$H NMR (DMSO-d$_6$, 300 MHz) δ 13.19 (s, 1H), 9.9 (s, 1H), 8.71 (m, 1H), 7.92 (d, 1H), 7.58 (m, 1H), 7.48 (m, 1H), 7.39 (d, 1H), 6.45 (s, 1), 6.02-5.99 (m, 2H), 5.82 (m, 2H), 5.6-4.92 (m, 3H), 4.29-4.24 (m, 2H), 3.95 (m, 4H), 3.79 (m, 2H), 3.4 (m, 2H), 3.15 (s, 1H), 3.01 (m, 4H), 2.5 (m, 1H), 1.9 (m, 2H), 1.71 (m, 1H), 1.44 (m, 1H).

Quinidium Pancratistatin 4-O-Phosphate (4l)

Off-white solid, 0.017 g, mpt. 180° C. (dec), $^1$H NMR (DMSO-d$_6$ 300 MHz) δ 13.22 (s, 1H), 9.9 (s, 1H), 8.71-8.69 (m, 1H), 7.94-7.91 (d, 1H), 7.57 (m, 1H), 7.40-7.37 (m, 2H), 6.45 (s, 1H), 6.02-5.99 (m, 3H), 5.73 (s, 1H), 5.16-5.13 (m, 3H), 4.25 (m, 2H), 3.94 (m, 4H), 3.77 (m, 4H), 3.35 (m, 4H), 3.01-2.97 (m, 1H), 2.19 (m, 1H), 1.83 (m, 1H), 1.67 (m, 2H), 1.13 (m, 1H). HRESI m/z found 730.2378 (M+H)$^+$, $C_{34}H_{41}N_3O_{13}P$ requires 730.2377 (M+H)$^+$.

Sodium Pancratistatin 3,4-cyclic Phosphate (5a)

Pancratistatin (0.2 g, 0.615 mmol) was dissolved in pyridine (8 ml) and heated to 80° C. under argon before adding tetrabutylammoniumdihydrogen phosphate (0.3 g, 1.47 equiv), dicyclohexylcarbodiimide (0.92 g, 4.44 mmol, 7.25 equiv). The reaction was stirred at 80° C. for 24 hours. $^1$H NMR of a crude sample of the reaction mixture showed a 50:50 mixture of 5a and starting material. Tetrabutylammonium dihydrogen phosphate (0.15 g) and dicyclohexylcarbodiimide (0.5 g) was added and the reaction continued for a further 24 hours. The reaction mixture was cooled and water (100 ml) was added. The dicyclohexylurea (DCU) precipitate was filtered off and the mother liquor concentrated to a white residue. Water was added to effect solution and the material was eluted on a Dowex 50W X 8-200 (Na$^+$ form) ion exchange resin. The UV active fractions were combined and concentrated to 5a, a beige crystalline solid 0.244 g, 96.8% yield. Mpt>300° C., $[α]_D^{25}$ -3.3° (c 0.54 H$_2$), R$_f$=0.63 (BuOH: MeOH:H$_2$O:NH$_4$OH 4:3:2:1). $^1$H NMR (DMSO-d$_6$, 300 MHz) δ 13.25 (s, 1H), 8.11 (s, 1H), 6.48 (s, 1H), 6.03-6.02 (m, 2H), 5.42 (bs, 1H), 4.69 (d, J=1H), 4.27-4.12 (m, 2H), 4.08-

4.03 (m, 3H), 2.85 (m, 1H). $^{13}$C NMR DMSO-$d_6$, 500 MHz). 169.2, 151.9, 145.4, 135.2, 131.6, 107.4, 101.7, 97.6, 75.5, 75.3, 69.4, 67.7, 50.5, 37.0 $^{31}$P NMR δ 13.22 ppm. HRFAB: m/2 Found 386.0267 (M−Na)$^-$, $C_{14}H_{13}O_{10}NP$ requires 386.02771 (M−Na)$^-$.

General Procedure for the Preparation of
Pancratistatin-3,4-Cyclic Phosphate Prodrugs
(5b-5c)

Sodium pancratistatin 3,4-cyclic phosphate (5a, 20 mg) was dissolved in water and the solution passed through a column (1×20 cm) of Dowex 50W X 8-200 bearing the respective cation. The UV active fractions were combined and freeze dried to give the corresponding pancratistatin 3,4-cyclic phosphate salt as a solid.

Lithium Pancratistatin 3,4-Cyclic Phosphate (5b)

Wt. 23.9 mg, Mpt=240° C., $^1$H NMR (DMSO-$d_6$, 300 MHz)*13.25 (s, 1H), 8.09 (s, 1H), 6.48 (s, 1H), 6.03-6.01 (m, 2H), 5.40 (bs, 1H), 4.69 (d, J=5.1 Hz, 1H), 4.27-4.22 (m, 2H), 4.11-4.03 (m, 3H), 2.87-2.83 (m, 1H).

Potassium Pancratistatin 3,4-Cyclic Phosphate (5c)

Wt. 17.8 mg, Mpt=238-248° C., $^1$H NMR (DMSO-$d_6$, 300 MHz)*13.25 (s, 1H), 8.11 (s, 1H), 6.48 (s, 1H), 6.03-6.01 (m, 2H), 5.41 (bs, 1H), 4.27-4.20 (m, 2H), 4.08-4.02 (m, 3H), 2.87-2.83 (m, 1H).

Dosages

The dosage of the presently disclosed compounds to be administered to humans and other animals requiring treatment will depend upon numerous factors, including the identity of the neoplastic disease; the type of host involved, including its age, health and weight; the kind of concurrent treatment, if any; the frequency of treatment and therapeutic ratio. Hereinafter are described various possible dosages and methods of administration, with the understanding that the following are intended to be illustrative only, and that the actual dosages to be administered, and methods of administration or delivery may vary therefrom. The proper dosages and administration forms and methods may be determined by one of skill in the art.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol 5 to about 1000 mg/k of host body weight.

Expressed in terms of concentration, an active ingredient may be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention may preferably be presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms may be prepared.

Powders may be prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules may be produced by preparing a powder mixture as hereinbefore described and filling into formed gelatin sheaths. Advantageously, as an adjuvant to the filling operation, a lubricant such as talc, magnesium stearate, calcium stearate and the like may be added to the powder mixture before the filling operation.

Soft gelatin capsules may be prepared by machine encapsulation of a slurry of active ingredients with a pharmaceutically acceptable carrier, such as vegetable oil, light liquid petrolatum or other inert oil or triglyceride.

Tablets may be made by preparing a powder mixture, granulating or slugging, adding a lubricant and pressing into tablets. The powder mixture may be prepared by mixing an active ingredient, suitably comminuted, with a diluent or base such as starch, lactose, kaolin, dicalcium phosphate and the like. The powder mixture may be granulated by wetting with a binder such as corn syrup, gelatin solution, methylcellulose solution or acacia mucilage and forcing through a screen. As an alternative to granulating, the powder mixture may be slugged, i.e., run through the tablet machine and the resulting imperfectly formed tablets broken into pieces (slugs). The slugs may be lubricated to prevent sticking to the tablet-forming dies by means of the addition of stearic acid, a stearic salt, talc or mineral oil. The lubricated mixture is then compressed into tablets.

Advantageously, the tablet may be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions may be prepared wherein each teaspoonful of composition contains a predetermined amount of an active ingredient for administration.

The water-soluble forms may be dissolved in an aqueous vehicle together with sugar, flavoring agents and preservatives to form a syrup. An elixir may be prepared by using a hydroalcoholic vehicle with suitable sweeteners together with a flavoring agent. Suspensions may be prepared of the insoluble forms with a suitable vehicle with the aid of a suspending agent such as acacia, tragacanth, methylcellulose and the like.

For parenteral administration, fluid unit dosage forms may be prepared utilizing an active ingredient and a sterile vehicle, water being preferred. The active ingredient, depending on the form and concentration used, may be either suspended or dissolved in the vehicle. In preparing solutions the water-soluble active ingredient may be dissolved in water for injection and filter sterilized before filling into a suitable vial or ampule and sealing. Advantageously, adjuvants such as a local anesthetic, preservative and buffering agents may be dissolved in the vehicle. Parenteral suspensions may be prepared in substantially the same manner except that an active ingredient may be suspended in the vehicle instead of being dissolved and sterilization cannot be accomplished by filtration. The active ingredient may be sterilized by exposure to ethylene oxide before suspending in the sterile vehicle. Advantageously, a surfactant or wetting agent may be included in the composition to facilitate uniform distribution of the active ingredient.

In addition to oral and parenteral administration, the rectal and vaginal routes may be utilized. The active ingredient may be administered by means of a suppository. A vehicle which has a melting point at about body temperature or one that is readily soluble may be utilized. For example, cocoa butter and various polyethylene glycols (Carbowaxes) can serve as the vehicle.

For intranasal installation, a fluid unit dosage form may be prepared utilizing an active ingredient and a suitable pharmaceutical vehicle, preferably purified water, a dry powder, may be formulated when insulation is the administration of choice.

For use as aerosols, the active ingredients may be packaged in a pressurized aerosol container together with a gaseous or liquefied propellant, for example, dichlorodifluoromethane, carbon dioxide, nitrogen, propane, and the like, with pharmaceutically acceptable adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention may be tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents may be prepared in such unit dosage form with the employment of pharmaceutical materials which themselves are available in the art and may be prepared by established procedures. The following preparations are illustrative of the preparation of potential unit dosage forms of the present invention, and not as a limitation thereof.

Composition "A"

Hard-Gelatin Capsules

One thousand two-piece hard gelatin capsules for oral use, each capsule containing 200 mg of an active ingredient may be prepared from the following types and amounts of ingredients:

| Active ingredient, micronized | 200 g |
|---|---|
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules have potential for use in treating a neoplastic disease by the oral administration of one or two capsules one to four times a day.

Using the procedure above, capsules could similarly be prepared containing an active ingredient in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, may be prepared by first suspending the compound in 0.5 ml of corn oil to render the material capsulatable and then encapsulating in the above manner.

The foregoing capsules have potential for use in treating a neoplastic disease by the oral administration of one or two capsules one to four times a day.

Composition "C"

Tablets

One thousand tablets, each containing 200 mg of an active ingredient, may be prepared from the following types and amounts of ingredients:

| Active ingredient, micronized | 200 g |
|---|---|
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets have potential for use in treating a neoplastic disease by the oral administration of one or two tablets one to four times a day.

Using the procedure above, tablets could similarly be prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, may be prepared from the following types and amounts of ingredients:

| Active ingredient, micronized | 10 g |
|---|---|
| Citric acid | 2 g |
| Benzoic acid | 1 g |
| Sucrose | 790 g |
| Tragacanth | 5 g |
| Lemon Oil | 2 g |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared has potential for use in treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, may be prepared from the following types and amounts of ingredients:

| Active ingredient, micronized | 30 g |
|---|---|
| POLYSORBATE 80 | 5 g |
| Methylparaben | 2.5 g |
| Propylparaben | 0.17 g |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared has potential for use in treating a neoplastic disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| Active ingredient, micronized | 15 g |
|---|---|
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories may be are inserted rectally or vaginally for treating a neoplastic disease.

Composition "G"

Intranasal Suspension

One liter of a sterile aqueous suspension for intranasal instillation, containing 20 mg of an active ingredient in each milliliter, may be prepared from the following types and amounts of ingredients:

| Active ingredient, micronized | 15 g |
|---|---|
| POLYSORBATE 80 | 5 g |
| Methylparaben | 2.5 g |
| Propylparaben | 0.17 g |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared has potential for use in treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form may be finely divided by means of an air micronizer. The micronized powder is then placed in a shaker-type container.

The foregoing composition has potential for use in treating a neoplastic disease, at localized sites by applying a powder one to four times per day.

Composition "I"

Oral Powder

One hundred grams of an active ingredient in bulk form may be finely divided by means of an air micronizer. The micronized powder is then divided into individual doses of 200 mg and packaged.

The foregoing powders have potential for use in treating a neoplastic disease, by the oral administration of one or two powders suspended in a glass of water, one to four times per day.

Composition "J"

Insulation

One hundred grams of an active ingredient in bulk form may be finely divided by means of an air micronizer.

The foregoing composition has potential for use in treating a neoplastic disease, by the inhalation of 300 mg one to four times a day.

It is of course understood that such modifications, alterations and adaptations as will readily occur to the artisan confronted with this disclosure are intended within the spirit of the present invention.

TABLE 1

Human Cancer Cell Line and Murine P-388 Lymphocytic Inhibitory Activities of Compounds 1a-b, 2a-b, 3a-b, 4a-l, 5a

| Compound | Leukemia P-388 | Pancreas-a BXPC-3 | Breast MCF-7 | CNS SF268 | Lung-NSC NCI-H460 | Colon KM20L2 | Prostate DU-145 |
|---|---|---|---|---|---|---|---|
| | $ED_{50}$ ($\mu$g/ml) | $GI_{50}$ ($\mu$g/ml) | | | | | |
| 1a | 0.017 | 0.02 | 0.023 | 0.014 | 0.032 | 0.025 | 0.015 |
| 1b | 0.24 | 0.20 | 0.20 | 0.079 | 0.19 | 0.17 | 0.026 |
| 2a | 0.013 | 0.0035 | 0.0032 | 0.0031 | 0.0084 | 0.0032 | 0.0032 |
| 2b | 0.012 | 0.069 | 0.059 | 0.047 | 0.058 | 0.06 | 0.031 |
| 3a | 0.0016 | 0.0019 | 0.00031 | 0.00055 | 0.0001 | 0.00037 | 0.00021 |
| 3b | 0.061 | 0.25 | 0.041 | 0.17 | 0.029 | 0.13 | 0.13 |
| 4a | 0.018 | 0.18 | 0.18 | 0.12 | 0.38 | 0.24 | 0.94 |
| 4b | 0.047 | 0.36 | 0.43 | 0.35 | 0.42 | 0.33 | 0.20 |
| 4c | 0.036 | 0.30 | 0.39 | 0.28 | 0.35 | 0.25 | 0.20 |
| 4d | 0.025 | 0.45 | 0.46 | 0.39 | 0.40 | 0.30 | 0.22 |
| 4e | 0.020 | 0.40 | 0.44 | 0.36 | 0.42 | 0.36 | 0.22 |
| 4f | 0.21 | 0.25 | 0.36 | 0.26 | 0.27 | 0.23 | 0.12 |
| 4g | 0.17 | 0.27 | 0.47 | 0.38 | 0.42 | 0.30 | 0.17 |
| 4h | 0.019 | 0.31 | 0.38 | 0.27 | 0.35 | 0.24 | 0.21 |
| 4i | 0.27 | 0.29 | 0.40 | 0.38 | 0.46 | 0.37 | 0.18 |
| 4j | 0.063 | 0.25 | 0.33 | 0.21 | 0.25 | 0.13 | 0.13 |
| 4k | 0.066 | 0.23 | 0.35 | 0.28 | 0.31 | 0.22 | 0.15 |
| 4l | 0.21 | 0.34 | 0.38 | 0.27 | 0.36 | 0.23 | 0.20 |
| 5a | 3.33 | 3.3 | 2.9 | 2.9 | 3.8 | 3.7 | 2.3 |

What we claim is:

1. A pharmaceutical composition comprising a compound having the structure wherein X is selected from the group consisting of: $Na^+$, $Li^+$ and $K^+$ and a pharmaceutically acceptable carrier therefor.

2. A pharmaceutical composition comprising a compound having the structure wherein X is selected from the group consisting of: 2 $Na^+$, 2 $H^+$, 2 $Li^+$, 2 $K^+$, $Mg^{2+}$, $Ca^{2+}$, $Zn^{2+}$, piperazine, morpholine, imidazole, quinine and quinidine and a pharmaceutically acceptable carrier therefor.

3. A method for treating cancer selected from the group consisting of leukemia, pancreatic cancer, breast cancer, central nervous system cancer, lung cancer, colon cancer and prostate cancer, comprising administering to a human or mammal afflicted with the cancer a pharmaceutically effective amount of the composition of claim 1.

4. A method for treating cancer selected from the group consisting of leukemia, pancreatic cancer, breast cancer, central nervous system cancer, lung cancer, colon cancer and prostate cancer, comprising administering to a human or mammal afflicted with the cancer a pharmaceutically effective amount of the composition of claim 2.

* * * * *